US012383580B2

(12) United States Patent
Ding et al.

(10) Patent No.: US 12,383,580 B2
(45) Date of Patent: Aug. 12, 2025

(54) MESENCHYMAL STEM CELL DERIVED EXOSOMES AND METHOD FOR PREVENTING OR TREATING A JOINT DISORDER BY ADMINISTERING A COMPOSITION COMPRISING THE SAME

(71) Applicant: BUDDHIST TZU CHI MEDICAL FOUNDATION, Hualien (TW)

(72) Inventors: Dah-Ching Ding, Hualien (TW); Kun-Chi Wu, Hualien (TW); Yu-Hsun Chang, Hualien (TW)

(73) Assignee: BUDDHIST TZU CHI MEDICAL FOUNDATION, Hualien (TW)

( * ) Notice: Subject to any disclaimer, the term of this patent is extended or adjusted under 35 U.S.C. 154(b) by 499 days.

(21) Appl. No.: 16/821,481

(22) Filed: Mar. 17, 2020

(65) Prior Publication Data

US 2020/0297761 A1    Sep. 24, 2020

(30) Foreign Application Priority Data

Mar. 18, 2019    (TW) .................. 108109188

(51) Int. Cl.
*A61K 35/12*    (2015.01)
*A61K 9/00*    (2006.01)
*A61P 19/02*    (2006.01)

(52) U.S. Cl.
CPC ............ *A61K 35/12* (2013.01); *A61K 9/0019* (2013.01); *A61P 19/02* (2018.01)

(58) Field of Classification Search
None
See application file for complete search history.

(56) References Cited

U.S. PATENT DOCUMENTS

| | | | |
|---|---|---|---|
| 2016/0220613 A1* | 8/2016 | Lim | ............ A61K 39/001 |
| 2017/0296590 A1 | 10/2017 | Cho et al. | |
| 2018/0296606 A1 | 10/2018 | Hogan et al. | |
| 2019/0290696 A1 | 9/2019 | De Miroschedji | |
| 2020/0188440 A1 | 6/2020 | Brodie et al. | |

FOREIGN PATENT DOCUMENTS

| WO | WO 2017/211906 A1 | 12/2017 |
|---|---|---|
| WO | WO 2018/211510 A1 | 11/2018 |

OTHER PUBLICATIONS

Lai et al. (2010) Stem Cell Res. 4: 214-222. (Year: 2010).*
Sze et al. (2007) Mol. Cell Proteomics 6, 1680-1689. (Year: 2007).*
Mendt et al. (2019) Bone Marrow Transplantation 54; 789-792. (Year: 2019).*
Mianehsaz et al. (2019) Stem Cell Research & Therapy 10: 340 (13 pages) (Year: 2019).*
Tao et al. (2017) Theronostics vol. 7, Issue 1: 180-195 (Year: 2017).*
Wang et al. (2017) Stem Cell Research & Therapy 8:189 (13 pages) (Year: 2017).*
Yaghoubi et al. (2019) Life Sciences 233: 116733 (10 pages) (Year: 2019).*
Zhang et al. (2016) Stem Cells International, vol. 2016 Article ID 1929536 (11 pages) (Year: 2016).*
Zhang et al. (2019) Biomaterials 200: 35-47. (Year: 2019).*
Zhu et al. (2017) Stem Cell Research & Therapy 8:64 (11 pages) (Year: 2017).*
Cosenza et al. "Mesenchymal Stem Cells Derived Exosomes and Microparticles Protect Cartilage and Bone from Degradation in Osteoarthritis," Scientific Reports, vol. 7, No. 16214, 12 pages, (2017).
Felson et al., "Osteoarthritis: New Insights. Part 1: The Disease and Its Risk Factors," Ann Intern Med., vol. 133, No. 8, p. 635-646, (2000); Abstract only.
Furuta et al. "Mesenchymal Stem Cell-Derived Exosokes Promote Fracture Healing in a Mouse Model," Stem Cells Translational Medicine, vol. 5, No. 12, p. 1620-1630, (2016).
Gilbert, J., "Current Treatment Options for the Restoration of Articular Cartilage," The American Journal of Knee Surgery, vol. 11, No. 1, p. 42-46, (1998); Abstract only.
Huňáková et al., "Role of Mesenchymal Stem Cells—Derived Exosomes in Osteoarthritis Treatment," Folia Veterinaria, vol. 62, No. 4, p. 19-23, (2018).
Johnson et al., "A Stem Cell-based Approach to Cartilage Repair," Science, vol. 336, No. 6082, p. 717-721, (2012); Abstract only.
Katsuda et al., "Potential Application of Mesenchymal Stem Cell-Derived Exosomes as a Novel Therapeutic Drug," Drug Delivery System, vol. 29, No. 2, p. 140-151, (2014); English abstract only.
Keller et al., "Embryonic Stem Cell Differentiation: Emergence of a New Era in Biology and Medicine," Genes & Development, vol. 19, p. 1129-1155 (2005).
Lee et al., "Effect of Glucosamine or Chondroitin Sulfate on the Osteoarthritis Progression: A Meta-analysis," Rheumatology International, vol. 30, No. 3, p. 357-363, (2010); Abstract only.
Li et al., "Stem Cell-Derived Extracellular Vesicles for Treating Joint Injury and Osteoarthritis," Nanomaterials, vol. 9, No. 261, 21 pages, (2019).
Liu et al. "MSC-derived Exosomes Promote Proliferation and Inhibit Apoptosis of Chondrocytes via lncRNA-KLF3-AS1/miR-206/GIT1 axis in Osteoarthritis," Cell Cycle, vol. 17, No. 21-22, p. 2411-2422, (2018).
Liu-Bryan et al., "Emerging Regulators of the Inflammatory Process in Osteoarthritis," Nat. Rev. Rheumatol., vol. 11, No. 1, p. 35-44, (2015).
Matsumoto et al., "Cartilage Repair in a Rat Model of Osteoarthritis Through Intraarticular Transplantation of Muscle-Derived Stem Cells Expressing Bone Morphogenetic Protein 4 and Soluble Flt-1," Arthritis & Rheumatism, vol. 60, No. 5, p. 1390-1405, (2009).

(Continued)

*Primary Examiner* — Russell G Fiebig
(74) *Attorney, Agent, or Firm* — Hoxie & Associates LLC (57) ABSTRACT

Provided is a pharmaceutical composition including an effective amount of mesenchymal stem cell derived exosomes. Also provided is a use of the pharmaceutical composition for preserving cartilage tissue, promoting cartilage regeneration and repairing damaged joints, thereby preventing or treating joint disorders in a subject in need thereof.

15 Claims, 6 Drawing Sheets
(3 of 6 Drawing Sheet(s) Filed in Color)

(56) References Cited

OTHER PUBLICATIONS

Murphy et al., "The Impact of Osteoarthritis in the United States: A Population-health Perspective," Am J Nurs., vol. 112, No. 3 Suppl 1, S13-9, (2012); Abstract only.
Richards et al., "Human Feeders Support Prolonged Undifferentiated Growth of Human Inner Cell Masses and Embryonic Stem Cells," Nature Biotechnology, vol. 20, No. 9, p. 933-936, (2002); Abstract only.
Sinusas et al., "Osteoarthritis: Diagnosis and Treatment," American Family Physician, vol. 85, No. 1, p. 49-56, (2012).
Thomson et al., "Embryonic Stem Cell Lines Derived from Human Blastocysts," Science, vol. 282, No. 5391, p. 1145-1147, (1998); Abstract only.
Toghraie et al., "Treatment of Osteoarthritis with Infrapatellar Fat Pad Derived Mesenchymal Stem Cells in Rabbit," The Knee, vol. 18, p. 71-75, (2011), 6 pages.
Toh et al., "MSC Exosome as a Cell-free MSC Therapy for Cartilage Regeneration: Implications for Osteoarthritis Treatment," Semin Cell Dev Biol., vol. 67, p. 56-64, (2017); Abstract only.
Versier et al., "Treatment of Knee Cartilage Defect in 2010," Orthopaedics & Traumatology: Surgery & Research, vol. 97, p. S140-S153, (2011).
Xu et al., "Feeder-free Growth of Undifferentiated Human Embryonic Stem Cells," Nature Biotechnology, vol. 19, p. 971-974, (2001); Abstract only.
Yin et al., "Human Umbilical Cord Mesenchymal Stem Cells and Exosomes: Bioactive Ways of Tissue Injury Repair," Am J Transl Res., vol. 11, No. 3, p. 1230-1240, (2019).
Zhang et al., "Exosomes from Human Umbilical Cord Mesenchymal Stem Cells Enhance Fracture Healing Through HIF-1α-mediated Promotion of Angiogenesis in a Rat Model of Stabilized Fracture," Cell Proliferation, vol. 52, No. 2, 12 pages, (2019).
Weiss & Troyer, "Stem Cells in the Umbilical Cord," *Stem Cell Rev.*, 2(2):155-162, (2006).
Rani, S., et al., "Mesenchymal Stem Cell-derived Extracellular Vesicles: Toward Cell-free Therapeutic Applications", Molecular Therapy, 23(5): 812-823 (2015).

\* cited by examiner

MESENCHYMAL STEM CELL DERIVED EXOSOMES AND METHOD FOR PREVENTING OR TREATING A JOINT DISORDER BY ADMINISTERING A COMPOSITION COMPRISING THE SAME

CROSS-REFERENCE TO RELATED APPLICATIONS

This application is a U.S. national application filed under 35 U.S.C. § 111 (a), which claims benefit to and priority of Taiwanese Patent Application No. 108109188, filed on Mar. 18, 2019, the contents of which are hereby incorporated by reference in its entirety.

BACKGROUND

1. Technical Field

The present disclosure relates to a pharmaceutical composition comprising exosomes of mesenchymal stem cells, and its use for preventing or treating joint disorders.

2. Description of the Related Art

Osteoarthritis (OA), also known as degenerative arthritis, is characterized by degradation and damage of articular cartilage, for example, changes in subchondral bone and osteophyte formation. OA is a common chronic degenerative joint disorder, affecting weight-bearing joints such as knees and hips of the older people. Statistics shows that more than 10% of American adults are clinically diagnosed with osteoarthritis, and it is the fourth most common cause of hospitalization, and also the most common cause of total knee and hip replacement surgery (Murphy, L. & Helmick, C G, The American Journal of Nursing, 112, S13-19 (2012)). The systemic factors susceptible to osteoarthritis include age, gender, ethnic group, bone density, estrogen supplementation, genetics, nutrition, etc., while local biomechanical factors include obesity, joint damage, joint deformity, exercise, muscle weakness, etc., leading to the deterioration of osteoarthritis (Felson, D T et al., Annals of Internal Medicine, 133, 635-646 (2000)).

In addition, osteoarthritis is not only a simple degenerative disease. Recent studies have found that low-grade inflammation not only increases the symptoms of the disease, but also accelerates the disease process. For example, activated macrophages and other innate immune cells release inflammatory cytokines that promote cartilage damage (Liu-Bryan, R. & Terkeltaub, R., Nat. Rev. Rheumatol., 11, 35-44, (2015)). Also, in synovial tissue taken from patients with osteoarthritis, an increased number of immune cells are found. These immune cells are related to the performance of pro-inflammatory cytokines including TNF-α, IL1β, IL6, IL8 and IL22. On the other hand, MMP1, MMP3, and MMP13 are directly responsible for the remodeling of the extracellular matrix.

Current treatments and therapies for osteoarthritis include drug treatment, non-drug treatment, surgical treatment, and so on.

Drug treatments for relieving osteoarthritis symptoms include acetaminophen, non-steroidal anti-inflammatory drugs, opioids, topical analgesics, corticosteroid injections, and hyaluronic acid injections (Sinusas, K., Am. Fam. Physician., 2012 Jan. 1; 85(1):49-56). Glucosamine and chondroitin sulfate also have certain protective effects (Lee, Y. H., Woo, J. H., Choi, S. J., Ji, J. D. & Song, G. G., Rheumatology International, 30, 357-363 (2010)). It is also found that drug treatment combined with non-drug interventional treatment is more effective in pain control. In addition, exercise is not only an effective interventional treatment, but also a method to prevent osteoarthritis. Other physical therapies include stents and foot aids.

Nevertheless, total joint replacement of knee, hip, and glenohumeral joints is still the most effective treatment, which can rescue joint function to near normal. However, since the damage of cartilage in osteoarthritis is usually serious, osteochondral transplantation, autotransplantation of perichondrium and periosteum, and chondrocyte transplantation may not be applicable (Gilbert, J. E., The American Journal of Knee Surgery, 11, 42-46 (1998), Versier, G., Dubrana, F. & French Arthroscopy, S., Orthopaedics & Traumatology, Surgery & Research: OTSR 97, S140-15 (2011)). Recently, the studies show that newly discovered kartogenin (KGN) may stimulate mesenchymal stem cells (MSCs) in cartilage tissue to differentiate into chondrocytes, and local administration of KGN in the early stage of osteoarthritis may improve the damaged joints (Johnson, K. et al., A stem cell-based approach to cartilage repair, Science 336, 717-721 (2012)).

Moreover, tissue engineering and stem cell therapy have also been applied in osteoarthritis research (Matsumoto, T. et al., Arthritis and Rheumatism, 60, 1390-1405 (2009); Toghraie, F. S. et al., The Knee, 18, 71-75 (2011)). Stem cell therapy may provide permanent biological treatment. All stem cells from various sources, such as embryonic stem cells (ESCs), induced pluripotent stem cells (iPSCs), and fetal and adult stem cells, have differentiation capability, and the stem cell therapy used to treat osteoarthritis depends on the capability of the stem cells to differentiate into cartilage. Therefore, the transplanted stem cells must be able to survive in diseased joints, and the self-renewal and differentiation capabilities of the stem cells are essential for regenerative medicine.

In recent years, extensive researches on stem cells have found that human embryonic stem cells (hESCs) and iPSCs can differentiate into almost all types of human cells and have the advantage of high self-renewal capability. In tissue engineering and regenerative medicine, hESCs are the most preferred for stem cell therapy, and have been applied in the treatments of many diseases, including Parkinson's disease, amyotrophic lateral sclerosis, spinal cord injury, stroke, heart disease, diabetes, hematopoietic disease, liver disease, and lung disease (Keller, G., Genes & Development, 19, 1129-1155, (2005)). Further, iPSCs have the potential for personal customization and thus is better than the ESCs.

Inevitably, the hESCs and iPSCs stem cell therapies have disadvantages. For example, human cells derived from stem cells have risks of forming teratoma and inducing immune response (Thomson, J. A. et al., Science, 282, 1145-1147 (1998)). On the other hand, mouse embryonic fibroblasts (MEFs) are the most commonly used as the feeding layer to maintain the growth of hESCs, while this culture method of hESCs is questioned owing to its non-human cell components, which may limit clinical applications to the human body. Although new methods for culturing hESCs and iPSC have been developed, such as methods of utilizing no feeding layer and serum and co-culturing with other human-derived cells, tumorigenicity still limits clinical applications of these stem cells (Xu, C. et al., Nature Biotechnology, 19, 971-974, (2001); Richards, M., Fong, C. Y., Chan, W. K., Wong, P. C. & Bongso, A., Nature Biotechnology, 20, 933-936 (2002)).

Furthermore, catabolic factors such as interleukin-1a and TNF-α existing in joints with osteoarthritis would inhibit stem cells to differentiate into chondrocytes, thereby reducing cartilage formation. Therefore, for repairing joints in patients, in addition to the introduction of cartilage, the reduction of inflammatory cytokines is equally important as well.

Therefore, the treatment of osteoarthritis still needs breakthrough, and further development of safe and effective therapies is needed.

SUMMARY

The present disclosure provides a pharmaceutical composition comprising exosomes of mesenchymal stem cells and its use for preventing or treating joint disorders. For example, the present disclosure provides a method of preventing or treating a joint disorder in a subject. The method comprises administering to the subject a pharmaceutical composition, wherein the pharmaceutical composition comprises a therapeutically effective amount of exosomes of mesenchymal stem cells.

In an embodiment of the present disclosure, the mesenchymal stem cell is an umbilical cord mesenchymal stem cell, a fetal mesenchymal stem cell, an umbilical cord blood mesenchymal stem cell, a placental mesenchymal stem cell, an amniotic fluid mesenchymal stem cell, a bone marrow mesenchymal stem cell, or an adipose mesenchymal stem cell. In another embodiment, the umbilical cord mesenchymal stem cell is a human umbilical cord mesenchymal stem cell. In yet another embodiment, the mesenchymal stem cell is not induced to differentiate. In an embodiment, the mesenchymal stem cell is an undifferentiated pluripotent mesenchymal stem cell. In another embodiment, the mesenchymal stem cell is at passage 3 to passage 6. In another embodiment, the exosomes are derived from the mesenchymal stem cell which is cultured in a serum-free medium.

In an embodiment of the present disclosure, the mesenchymal stem cell presents at least one of the cell surface markers of CD44, CD73, CD90, CD105, and HLA-ABC. In another embodiment, the mesenchymal stem cell does not present the cell surface markers of CD34, CD45, CD56, and HLA-DR. In another embodiment, the mesenchymal stem cell presents the cell surface markers of CD44, CD73, CD90, CD105, and HLA-ABC, and does not present the cell surface markers of CD34, CD45, CD56, and HLA-DR.

In an embodiment, the subject is human. In another embodiment, the joint disorder is articular cartilage defect, osteoarthritis, chronic joint rheumatism, deformity arthritis, scapulohumeral periarthritis, cartilage degeneration, or anterior cruciate ligament damage. In another embodiment, the joint disorder is osteoarthritis. In an embodiment, the pharmaceutical composition is administered to the subject by injection.

In an embodiment, the pharmaceutical composition repairs damaged joint, preserves cartilage tissue, or promotes cartilage regeneration, thereby preventing or treating the joint disorders.

In an embodiment, a subject treated with the pharmaceutical composition of the present disclosure for preventing or treating a joint disorder has a thicker cartilage tissue than those without the treatment of the pharmaceutical composition of the present disclosure. In another embodiment, the thickness of the cartilage tissue of a subject treated with the pharmaceutical composition of the present disclosure for preventing or treating a joint disorder is at least 2 times than those without such treatment. In yet another embodiment, the thickness of the cartilage tissue of a subject treated with the pharmaceutical composition of the present disclosure for preventing or treating a joint disorder is 2.5 times or more than those of such treatment.

In an embodiment of the present disclosure, the exosomes in the pharmaceutical composition are produced by $1\times10^7$ to $1\times10^9$ mesenchymal stem cells. In another embodiment, the exosome presents at least one of the cell surface markers of CD9, CD63 and CD81. In another embodiment, the exosome does not present the cell surface marker of GM130. In another embodiment, the exosome presents the cell surface markers of CD9, CD63 and CD81, and does not present the cell surface marker of GM130.

BRIEF DESCRIPTION OF THE DRAWINGS

The patent or application files contains at least one drawing executed in color. Copies of this patent or patent application publication with color drawing(s) will be provided by the Office upon request any payment of the necessary fee.

FIGS. 3A to 3D show the cell surface markers and the differentiation capability of human umbilical cord mesenchymal stem cells. FIG. 3B: Human umbilical cord mesenchymal stem cells cultured after 14 days present oil red O-positive staining, indicating the development of adipocytes; FIG. 3C: Human umbilical cord mesenchymal stem cells cultured after 14 days present alizarin red staining, indicating the development of osteocytes.

DETAILED DESCRIPTION OF THE EMBODIMENTS

Mesenchymal stem cells (MSCs) include various types derived from different sources, e.g., bone marrow-mesenchymal stem cells (BM-MSCs), umbilical cord blood-mesenchymal stem cells (UCB-MSCs), human umbilical cord mesenchymal stem cells (HUCMSCs), adipose tissue-derived stem cells (ADSCs), muscle-derived stem cells (MDSCs), and dental pulp stem cells (DPSCs), and have been used as stem cell therapy for chondrocyte regeneration. Among them, the bone marrow-mesenchymal stem cells, adipose tissue-derived mesenchymal stem cells, and muscle-derived stem cells are abundant and can be isolated from adults at risk for osteoarthritis. Therefore, those mesenchymal stem cells have the potential for the stem cell therapy of arthritis.

In addition to direct differentiation into chondrocytes to repair damaged osteoarthritis joints, paracrine effects of the mesenchymal stem cells have important anti-inflammatory and immunosuppressive effects on immune cells. Mesenchymal stem cells interact with T cells and inhibit the proliferation of native T lymphocytes and the differentiation into Th1 or Th17 phenotypes. Both environmentally soluble and contact-dependent signals can trigger the therapeutic effect of the mesenchymal stem cells. Therefore, various interleukins and extracellular vesicles (EVs) secreted by the mesenchymal stem cells to the extracellular environment are important in osteoarthritis treatment.

Extracellular vesicles are important mediators of intercellular communication, which not only participate in normal physiological functions, but also affect the occurrence and development of diseases. Exosomes are a type of extracellular vesicle with a diameter of 40 to 100 nanometers (nm), and can be separated by centrifugation from all types of body fluids, including blood, urine, bronchoalveolar lavage fluid, breast milk, amniotic fluid, synovial fluid, pleural exudate, ascites, etc. In addition, there is no specific marker on the exosomes.

Mesenchymal stem cell-derived extracellular vesicles (MSC-EV) can be stored, without losing their original functions, and have safety. Therefore, mesenchymal stem cell-derived extracellular vesicles can be an alternative acellular therapy to replace the direct transplantation of mesenchymal stem cells. Mesenchymal stem cell-derived extracellular vesicles have been studied in various animal models of cardiovascular disease, acute kidney or liver injury, lung injury, and skin wound healing (Rani, S. et. al., Mol. Ther., 23, 812-823, (2015)). However, there have been no studies on mesenchymal stem cell-derived extracellular vesicles in osteoarthritis model.

The animal model that represents the pathogenesis of osteoarthritis is very important for the development of new therapies. The model must mimic the clinical and pathological changes related to the joints of patients. In the present disclosure, a rabbit model of osteoarthritis with anterior cruciate ligament transection (ACLT) is used. This model has been used to find the cause of osteoarthritis, and also used in researches of osteoarthritis therapy including stem cell therapy. However, this animal model has not been studied for the exosome therapy.

The following is a description of the implementation of the present disclosure through embodiments. Those skilled in the art can easily understand the advantages and effects of the present disclosure from the content disclosed in the description. This disclosure can also be implemented or applied through other different implementations. The details in this specification can also be based on different perspectives and applications, and given different modifications and changes without departing from the spirit of this disclosure. The following implemented examples should be understood as illustrative only, and should not be construed to limit the present disclosure.

Example 1: Establishing an Animal Model

Twelve 14-month-old New Zealand White (NZW) rabbits were used in this example. Rabbit knee joints were divided into two groups: (1) the OA group: induced osteoarthritis without treatment, n=6; and (2) the experimental group (OA+EXO): induced osteoarthritis with treatment of exosomes, n=6.

All rabbits were anesthetized by intramuscular injection of ketamine (100 mg/kg) and xylazine (8 mg/kg). Both knees were shaved and disinfected with iodine (Betadine). A medial patella incision was percutaneously made, and arthrotomy was performed to displace patella laterally for the knees to fully flex. Anterior cruciate ligament (ACL) was cut transversely with a 15-gauge blade, and the joint was rinsed with sterile saline before suturing. The joint capsule and synovial membrane were sutured together with 4-0 polypropylene sutures, and the skin was sutured with 3-0 nylon sutures. All rabbits were sent back to the cage after surgery, and allowed to move freely, with administration of 0.2 mg/kg/day of meloxicam orally for 7 days to relieve pain.

Two months after the anterior cruciate ligament transection, the changes of knee joints in rabbits in each group were examined in the following manner.

First, the joint surface was checked with the naked eye. After the rabbit was euthanized, the surfaces of the distal femur and the proximal tibia were exposed and examined visually. 2 mL of Indian ink was injected onto the tibial plateau with a syringe. After 2 minutes, the surface was washed with saline, and staining pattern of tibial plateau was observed with the naked eye. The results were shown in FIG. 1. The inner side of cartilage in the OA group showed severe cartilage damage (as indicated by an arrow), and the knee joint of the OA group showed significant cartilage damage (as indicated by the arrow).

Figure 6:
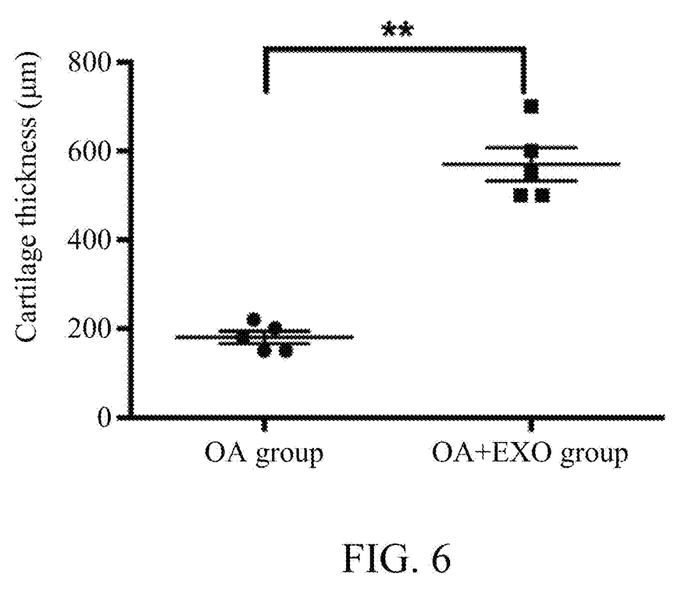
FIG. 6 shows the comparison of cartilage thickness between the OA group without exosome repair and the OA+EXO group with exosome repair, ** $p<0.01$, using Mann-Whitney test for comparison (n=5).

The tissue changes were directly observed with a microscope, and the cartilage damage part was randomly taken to measure the thickness at six sites. The results were shown in the OA group illustrated in FIG. 6. All data in FIG. 6 were expressed as medians and ranges.

The histological evaluation method was as follows: the distal femur and proximal tibia plateau were removed, and fixed with 10% buffered formalin (Sigma) for 48 hours; and the specimen was decalcified with 10% EDTA (Gibco, Grand Island, NY, USA) for 2 weeks, and cut into 4 pieces. All sections were embedded in paraffin, and then successive sagittal sections were prepared and stained with hematoxylin & eosin (H&E; Sigma) and safranin O (Sigma).

Immunohistochemical analysis was performed in the following manner: 2 distal femurs of each group were obtained and immediately embedded in optimal cutting temperature (OCT) compounds (Miles, Elkhart, IN), quickly frozen in liquid nitrogen, and stored at −80° C. until use.

After rehydration of femoral joint sections, endogenous peroxidase was blocked with 3% hydrogen peroxide (Sigma), and then treated with a mixture of 2.5% hyaluronidase (Sigma) and 1 mg/mL of streptomycin (Pronase) in PBS (pH 7.4; Sigma) at 37° C. for 1 hour to recover type II collagen. Further, type X collagen was recovered at 37° C. using 0.1 units/mL of chondroitinase ABC (Sigma) for 1 hour, and then treated with 1 mg/mL pepsin (Sigma) in Tris-HCl (pH 3.0, MDBio, Taipei, Taiwan) at 37° C. for 15 minutes. Next, the sections were blocked using Ultra V Block (Thermo Scientific, Fremont, CA) for 10 minutes, and reacted with a primary antibody (type II collagen was reacted with mouse monoclonal antibody (1:200) (CP18;

Calbiochem, La Jolla, CA); and type X collagen was reacted with rat multiple antibody (1:200) (ab58632; Abcam, Cambridge, MA)) at 37° C. for 4 hours.

After reacting with a secondary antibody (type II collagen was reacted with biotin-labeled goat anti-mouse immunoglobulin (Dako, Carpinteria, CA), and type X collagen was reacted with biotin-labeled goat anti-mouse immunoglobulin (Biocare Medical, Walnut Creek, CA)) for 30 minutes, a reaction using horseradish peroxidase-conjugated streptavidin (Biocare Medical) was performed.

After stained with 3,3-diamine benzidine solution containing 0.01% hydrogen peroxide, sections were counterstained with hematoxylin (Sigma), and a ratio of stained areas of the type II collagen and type X collagen of articular cartilage in each femur to total areas was measured using Image-Pro Plus version 5.0 software.

Figure 2:
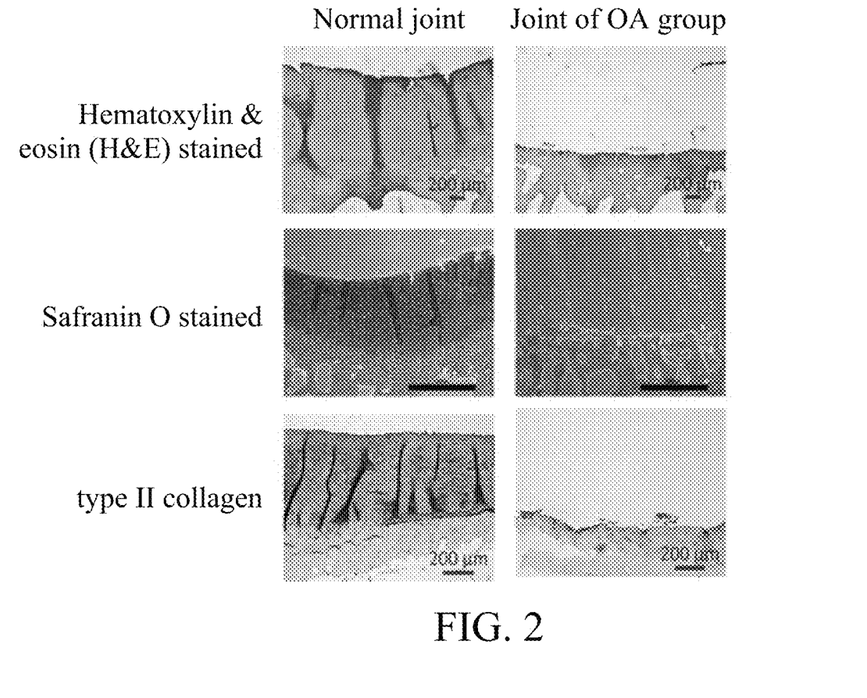
FIG. 2 shows the results of histological evaluation and immunohistochemical analysis of knee joints of the normal group and the OA group.

The results were shown in FIG. 2. H&E staining, safranin O staining, and immunohistochemical analysis of type II collagen showed that the joints in the OA group had significant cartilage damage, implying that this animal model can mimic the pathogenesis of OA and present similar disease characteristics. Therefore, the animal model can be used as a model to effectively evaluate OA therapy.

Example 2: Expansion of Human Umbilical Cord Mesenchymal Stem Cells (HUCMSCs)

The method of obtaining and using human umbilical cord was approved by the Human Test Committee of Buddhist Tzu Chi General Hospital (IRB 100-166). This experimental method was performed according to the Declaration of Helsinki, and was approved by the local ethics review committee. Written informed consents of all subjects were obtained before the experiment. The detailed method for obtaining human umbilical cord mesenchymal stem cells is known in the art, and the specific implementation of this embodiment is as follows.

Briefly, human umbilical cord specimens (20 cm in length and 20 g in weight) were collected in sterile boxes containing Hankpin's balanced salt solution (Gibco/BRL 14185-052, Grand Island, NY, USA), and Wharton's jelly (WJ) was isolated from blood vessels and amnion in 24 hours.

First, the human umbilical cord was washed for three times with $Ca^{2+}$ and $Mg^{2+}$-free phosphate buffered saline (PBS, Biowest, Nuaille, France), and then cut with scissors in the midline direction. The vessels of the umbilical artery, vein and outlining membrane were dissociated from Wharton's jelly. The Wharton's jelly was then cut into pieces smaller than 0.5 $cm^3$, treated with type I collagenase (Sigma, St. Louis, MO, USA) and incubated at 37° C. in a humidified environment with 95% air and 5% $CO_2$ for 14 to 18 hours.

The above explants were then incubated at 37° C. in a low-glucose Dulbecco's modified Eagle's medium (DMEM; LG, Sigma) containing 10% fetal bovine serum (FBS; Biological Industries, Kibbutz Beit Haemek, Israel) and antibiotics, and cultured in a humidified environment with 95% air and 5% $CO_2$. They were left undisturbed for 5 to 7 days to allow for migration of cells from the explants. The obtained human umbilical cord mesenchymal stem cells were designated as passage 1. The medium was changed twice a week, and the cells were passaged when 90% of confluence was reached.

Example 3: Characteristics and Differentiation Capability of Human Umbilical Cord Mesenchymal Stem Cells (HUCMSCs)

The surface molecular characteristics of human umbilical cord mesenchymal stem cells cultured on passage 3 or 4 were measured by flow cytometry. Cells were detached using Accutase (Millipore, Billerica, MA, USA) in PBS, and washed with PBS containing 2% fetal bovine serum albumin (Sigma) and 0.1% sodium azide (Sigma). Next, they were incubated with respective antibodies conjugated with fluorescein isothiocyanate or phycoerythrin, including CD29, CD34, CD44, CD45, CD56, CD73, CD90, CD105, HLA-ABC, and HLA-DR (BD PharMingen, Franklin Lakes, NJ, USA), and then were analyzed using a flow cytometer (Becton Dickinson, San Jose, CA, USA).

Figure 3A:
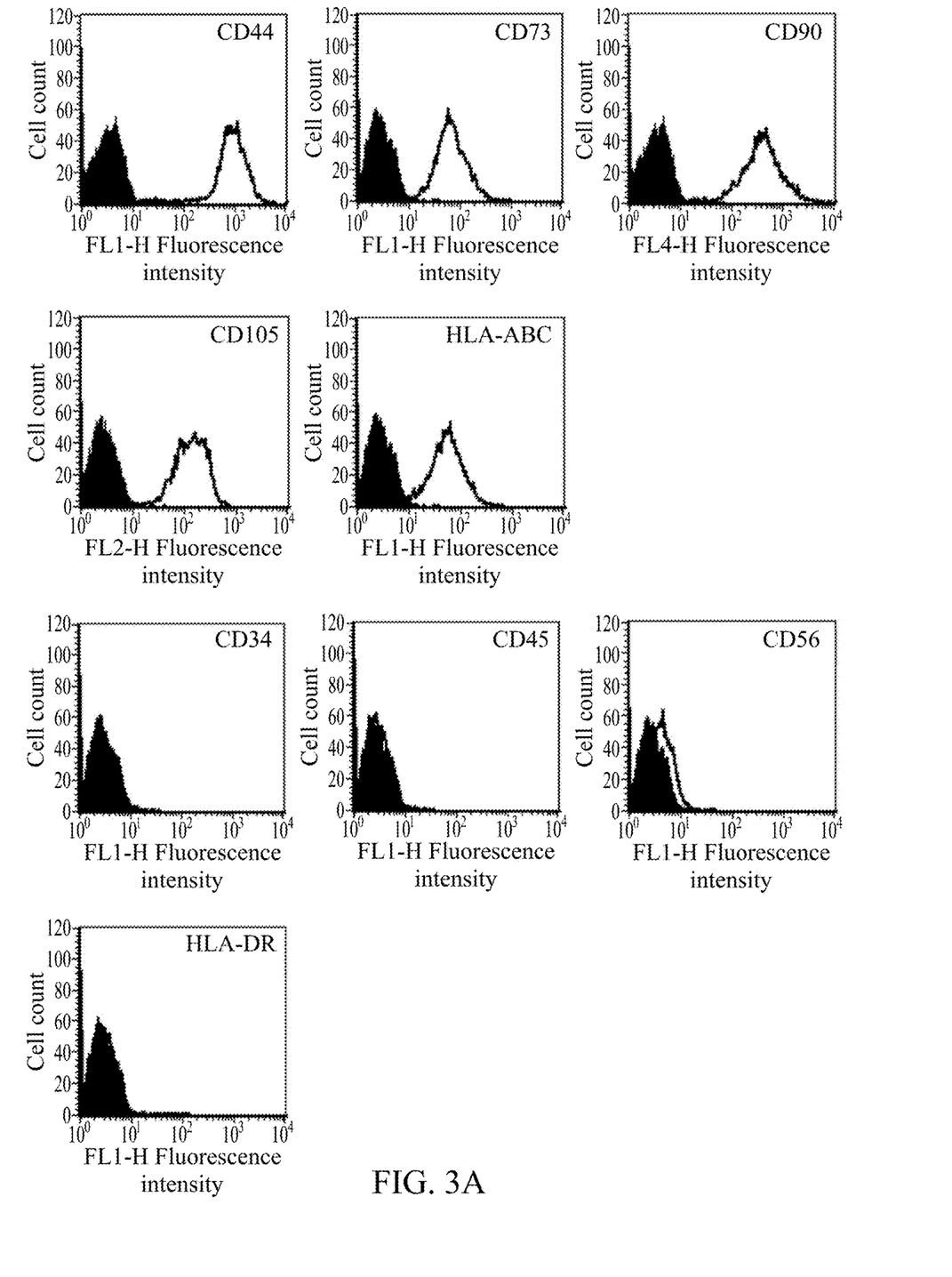
FIG. 3A: The analysis result of human umbilical cord mesenchymal stem cells at passage 3 by flow cytometry shows that the cells present cell surface markers CD44, CD73, CD90, CD105 and HLA-ABC, but do not present cell surface markers CD34, CD45, CD56 and HLA-DR.

As shown in FIG. 3A, the cell surface markers presented by human umbilical cord mesenchymal stem cells were CD44, CD73, CD90, CD105, and HLA-ABC, while the unpresented cell surface markers were CD34, CD45, CD56, and HLA-DR.

The capability of human umbilical cord mesenchymal stem cells to differentiate into adipocytes was tested by means of inducing adipogenesis. A total of $5\times10^4$ human umbilical cord mesenchymal stem cells were seeded onto a 12-well plate with an adipogenic medium (DMEM added with 10% FBS, 5 µg/mL insulin, 0.5 mmol/L isobutyl methylxanthine, 1 µmol/L dexamethasone, and 60 µmol/L indomethacin, all compounds being purchased from Sigma). Human umbilical cord mesenchymal stem cells were cultured in an adipogenic medium for 14 days, and the medium was changed every 3 days. After differentiation for 14 days, the differentiated adipocytes were stained with oil red O (Sigma) and photographed.

Figure 3B:
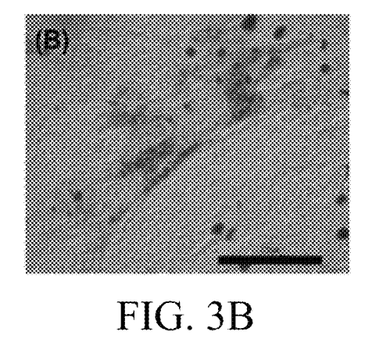

The result was shown in FIG. 3B. The differentiated human umbilical cord mesenchymal stem cells showed large oil red O-positive droplets in the cytoplasm.

The capability of human umbilical cord mesenchymal stem cells to differentiate into osteocytes was tested by means of induction. A total of $1\times10^4$ human umbilical cord mesenchymal stem cells were seeded into each one well of a 12-well plate with an osteogenic medium (DMEM added with 10% FBS, 0.1 µmol/L dexamethasone, 10 mmol/L β-glyceryl phosphate, and 50 µmol/L ascorbic acid). The medium was changed every 3 days. After differentiation for 14 days, osteocytes were stained with alizarin red (Sigma) and photographed.

Figure 3C:
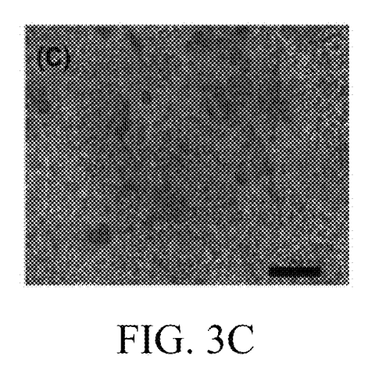

As shown in FIG. 3C, the cell morphology of the differentiated human umbilical cord mesenchymal stem cells was transformed into a cuboid shape, and the alizarin red staining was positive.

The chondrogenic capability of human umbilical cord mesenchymal stem cells was tested by micromass culture. Human umbilical cord mesenchymal stem cells were seeded in a total volume of 30 µL onto the bottom of a dry 15-mL test tube (BD Pharmingen) at a density of $25\times10^6$ cells/mL, and placed in a $CO_2$ incubator of humidified environment at 37° C. for 2 hours. Each tube was added with an additional chondrogenic medium (0.75 mL). The medium was changed every 48 hours. After 3 weeks of culture, micromass cartilages were formed. The micromass cartilages were collected and photographed. Then, the micromass cartilages were fixed at 4° C. with 4% paraformaldehyde for 24 hours. After washed with PBS, they were then transferred to 70% ethanol, and processed for histology. The paraffin sections (5 µm) were assessed for cartilage by aggrecan (1:100, GeneTex, Irvine CA, USA) immunohistochemistry (IHC) staining.

Figure 3D:
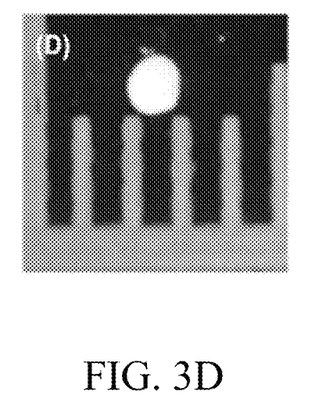
FIG. 3D: Human umbilical cord mesenchymal stem cells cultured in chondrogenic medium for 3 weeks gather into clumps, indicating the development of chondrocytes; scale bar=100 μm.

The result was shown in FIG. 3D. After 21 days of chondrogenic induction, human umbilical cord mesenchymal stem cells conglobulated into clusters, and became positive for aggrecan staining.

The above results showed that human umbilical cord mesenchymal stem cells can differentiate into adipocytes, osteocytes and chondrocytes.

Example 4: Purification of Human Umbilical Cord Mesenchymal Stem Cells (HUCMSCs) Derived Exosomes Exosomes of MSC-EV will be purified from the human umbilical cord mesenchymal stem cells conditioned media (CM) using HPLC, as described earlier (Lai, R. C. et al., Stem Cell Res., 4, 214-222, (2010); Sze, S. K. et al., Mol. Cell Proteomics, 6, 1680-1689, (2007)). Briefly, the method of preparing the conditioned medium was as follows: human umbilical cord mesenchymal stem cells cultured to 80% confluence at passages 3 to 6 were washed three times with PBS and cultured overnight in a chemically defined medium. The medium was composed of DMEM low glucose without phenol red (Invitrogen), insulin, transferrin, selenoprotein (Insulin-Transferrin-Selenium, ITS; Invitrogen), 5 ng/mL FGF2 (Invitrogen), 5 ng/mL PDGF AB (Peprotech, Rocky Hill, NJ), glutamic acid-penicillin-streptomycin, and β-mercaptoethanol. Then, the culture was washed three times with PBS, and a fresh chemically defined medium was added. After 3 days, the medium was collected and centrifuged at 500×g, and the supernatant was filtered using a 0.2 μm filter. No serum was used in the preparation of the conditioned medium, and the cells were not induced for differentiation. Serum-free conditioned medium collected from human umbilical cord mesenchymal stem cell cultures was concentrated 50-fold by tangential flow filtration using a membrane with a 100 kDa MWCO (molecular weight cut off) (Sartorius, Goettingen, Germany).

The concentrated conditioned medium was collected and centrifuged at 3000×g for 15 minutes to remove cells and cell debris. The supernatant was transferred to a sterile container, added with an appropriate volume of ExoQuick-TC (System Biosciences, Palo Alto, CA, USA), and mixed by inverting or flicking the container before refrigerating at 4° C. overnight (at least 12 hours). The container was kept upright during the incubation period without rotating or mixing. The ExoQuick-TC/conditioned medium mixture was centrifuged at 1500×g for 30 minutes. Centrifugation can be performed at room temperature or 4° C. After centrifugation, exosomes may appear as beige or white pellets at the bottom of the container. With suctioning the supernatant, it was centrifuged at 1500×g for 5 minutes; after concentrating the residual ExoQuick-TC solution, all remaining liquid was removed by suction. The precipitated exosome mass should not be disturbed. The precipitation of exosomes was resuspended in 100 to 500 μL of sterile 1×PBS for injection into the joints.

A micro-bicinchoninic acid assay (Thermo Fisher Scientific, Dreieich, Germany) was used to determine the protein concentration of the exosome samples, and the purified exosomes were determined by the Western blot method. 5 μg of the concentrated exosome fractions were treated with a sample buffer (dithiothreitol, 0.1% SDS, 0.1 M Tris-HCl; pH 7.0), and boiled at 95° C. for 5 minutes before separating with 12% SDS-PAGE electrophoresis. The samples were transferred to a PVDF membrane (Merck Millipore, Darmstadt, Germany) and antibodies that recognize exosomal marker proteins CD9, CD63 and CD81 (BD Biosciences) or a negative marker GM130 (Sigma-Aldrich) were used.

Figure 4:
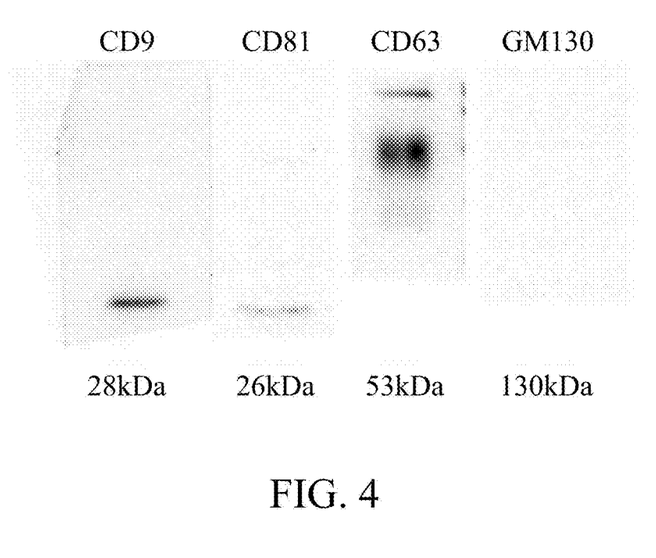
FIG. 4 shows the cell surface markers on the exosome purified from human umbilical cord mesenchymal stem cells, which present cell surface markers CD9, CD63 and CD81, but not the cell surface marker GM130.

The results were shown in FIG. 4. The exosomes of human umbilical cord mesenchymal stem cells purified by the above method showed typical characteristics of cell surface markers of exosomes, including CD9, CD63, and CD81, while GM130 was negative.

Figure 1:
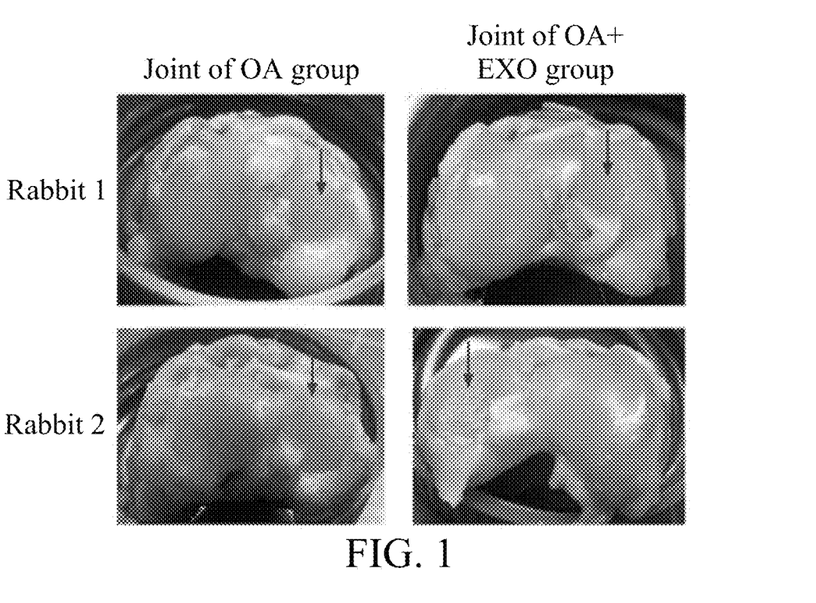
FIG. 1 shows the joints of animal models of the OA group which is not treated with exosomes and the OA+EXO group which is treated with exosomes by visual inspection. The arrows indicate cartilage damage in the joints.

Example 5: Repair with Human Umbilical Cord Mesenchymal Stem Cells (HUCMSCs) Derived Exosomes At eight weeks after ACLT surgery, the knee joints of the OA+EXO group were injected with 0.4 mL of exosomes. After 12 weeks for the EXO treatment, the rabbits in each group were sedated with 15 to 40 mg/kg pentobarbital (3%) and sacrificed after $CO_2$ inhalation. Visual inspection found that knee cartilage in the OA+EXO group repaired with exosomes showed less cartilage damage (FIG. 1).

Figure 5A:
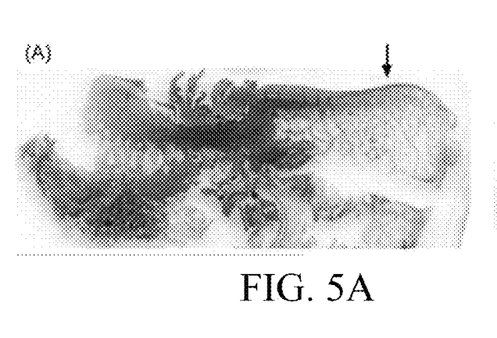
FIGS. 5A to 5F show the results of immunohistochemical analysis of aggrecan in the joints of the OA group (FIGS. 5A, 5C and 5E) without exosome repair and the OA+EXO group (FIGS. 5B, 5D and 5F) with exosome repair at different magnifications. The scale bar of FIGS. 5C and 5D is 1000 μm, and the scale bar of FIGS. 5E and 5F is 100 μm. The arrow indicates the inner side of the cartilage where osteoarthritis occurs.
Figure 5B:
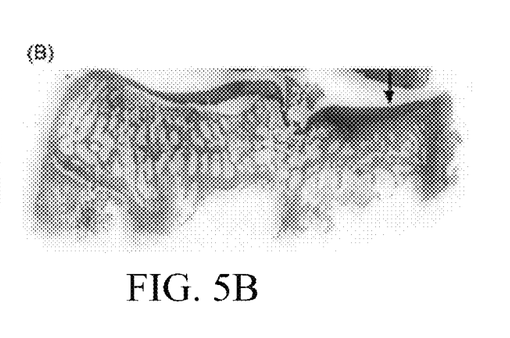
Figure 5C:
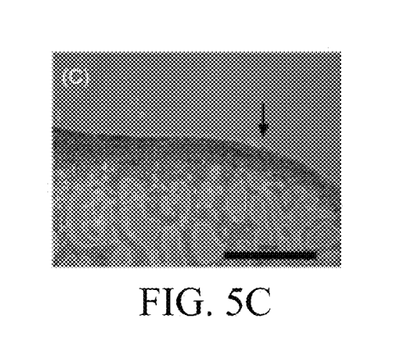
Figure 5D:
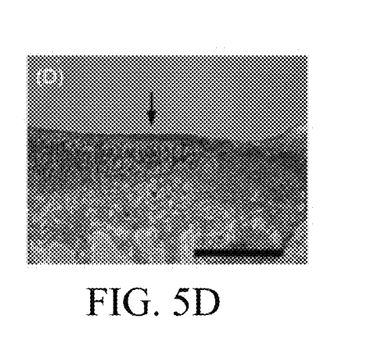
Figure 5E:
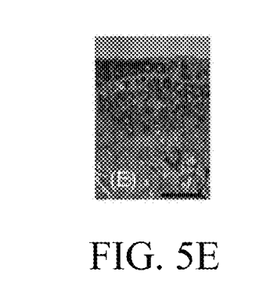
Figure 5F:
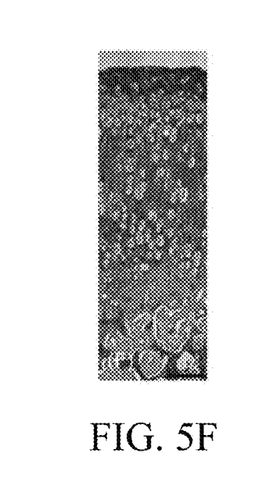

The above-mentioned immunohistochemical analysis was used to examine the aggrecan content of knee cartilage in each group. The results were shown in FIGS. 5A to 5F. As compared with the OA group (FIGS. 5A, 5C and 5E), the OA+EXO group (FIGS. 5B, 5D and 5F) repaired with exosomes contains significantly more aggrecan on the inner side of cartilage. The cartilage thickness of the OA+EXO group (FIG. 5F) repaired with exosomes was 2.5 times than that of the OA group (FIG. 5E) without exosome repair.

In the example, the cartilage damage part of each group was randomly taken to measure the thickness at six sites. After the measurement, the statistics were performed in the following method, and the results were shown in FIG. 6. All data shown in FIG. 6 were expressed as median and range, and statistical comparisons for histopathological grade were performed using non-parametric tests (such as the Mann-Whitney U test). When the p-value was <0.05, the difference was considered significant. All statistical analyses were performed using SSPS. The results showed that there was a significant difference in cartilage thickness between the OA+EXO group and the unrepaired OA group.

The above implementation examples are only illustrative of, instead of limiting, the present disclosure. Those skilled in the art can make appropriate modifications and changes to the above implementation examples without departing from the spirit and scope of this disclosure. Therefore, the scope of protection of this disclosure should be as listed in the claims of this disclosure as follows.

What is claimed is:

1. A method for treating a joint disorder in a subject in need thereof, comprising administrating a pharmaceutical composition comprising an effective amount of exosomes derived from mesenchymal stem cells to the subject, wherein the mesenchymal stem cell is an umbilical cord mesenchymal stem cell and wherein the joint disorder is cartilage degradation or anterior cruciate ligament injury.

2. The method of claim 1, wherein the mesenchymal stem cell is an undifferentiated mesenchymal stem cell.

3. The method of claim 1, wherein the mesenchymal stem cell presents at least one of cell surface markers of CD44, CD73, CD90, CD105 and HLA-ABC.

4. The method of claim 1, wherein the mesenchymal stem cell does not present cell surface markers of CD34, CD45, CD56 and HLA-DR.

5. The method of claim 1, wherein the mesenchymal stem cell presents cell surface markers of CD44, CD73, CD90, CD105 and HLA-ABC, and does not present cell surface markers of CD34, CD45, CD56 and HLA-DR.

6. The method of claim 1, wherein the umbilical cord mesenchymal stem cell is a human umbilical cord mesenchymal stem cell.

7. The method of claim 1, wherein the mesenchymal stem cell is at passage 3 to passage 6.

8. The method of claim 7, wherein the exosomes are derived from the mesenchymal stem cell cultured in a serum-free medium.

9. The method of claim 1, wherein the exosomes present at least one of cell surface markers of CD9, CD63, and CD81.

10. The method of claim 1, wherein the exosomes do not present a cell surface marker of GM130.

11. The method of claim 1, wherein the exosomes present cell surface markers of CD9, CD63 and CD81, and do not present a cell surface marker of GM130.

12. The method of claim 1, wherein the pharmaceutical composition preserves cartilage tissue to treat the joint disorder.

13. The method of claim 1, wherein the pharmaceutical composition promotes cartilage regeneration to treat the joint disorder.

14. The method of claim 1, wherein the pharmaceutical composition is administered by injection to the subject.

15. The method of claim 1, wherein the joint disorder is anterior cruciate ligament injury.

* * * * *